(12) United States Patent
Meulink et al.

(10) Patent No.: US 10,136,933 B2
(45) Date of Patent: Nov. 27, 2018

(54) ORTHOPEDIC CONNECTIONS

(71) Applicant: Zimmer, Inc., Warsaw, IN (US)

(72) Inventors: Steven L. Meulink, Warsaw, IN (US); Paul J. Conrad, West Chester, OH (US)

(73) Assignee: Zimmer, Inc., Warsaw, IN (US)

( * ) Notice: Subject to any disclaimer, the term of this patent is extended or adjusted under 35 U.S.C. 154(b) by 708 days.

(21) Appl. No.: 14/063,725

(22) Filed: Oct. 25, 2013

(65) Prior Publication Data

US 2014/0121713 A1 May 1, 2014

Related U.S. Application Data

(60) Provisional application No. 61/720,064, filed on Oct. 30, 2012, provisional application No. 61/740,088, filed on Dec. 20, 2012.

(51) Int. Cl.

| *A61B 17/04* | (2006.01) |
|---|---|
| *A61B 17/86* | (2006.01) |
| *A61F 2/08* | (2006.01) |
| *A61F 2/36* | (2006.01) |
| A61F 2/30 | (2006.01) |
| A61F 2/40 | (2006.01) |

(52) U.S. Cl.
CPC ........ *A61B 17/8685* (2013.01); *A61B 17/863* (2013.01); *A61F 2/3609* (2013.01);
(Continued)

(58) Field of Classification Search
CPC .. A61F 2/3609; A61F 2002/365; A61B 17/84; A61B 17/8625; A61B 17/863; A61B 17/8685; F16B 33/02
(Continued)

(56) References Cited

U.S. PATENT DOCUMENTS

| 4,917,530 A | * | 4/1990 | Engelhardt | ........... | A61F 2/3609 |
|---|---|---|---|---|---|
| | | | | | 403/334 |
| 5,549,703 A | * | 8/1996 | Daigle | ................... | A61F 2/3609 |
| | | | | | 623/22.43 |

(Continued)

FOREIGN PATENT DOCUMENTS

| DE | 4405447 A1 | 8/1995 |
|---|---|---|
| DE | 10045678 C1 | 2/2002 |

(Continued)

OTHER PUBLICATIONS

"European Application Serial No. 13786853.5, Office Action dated Jul. 2, 2015", 2 pgs.

(Continued)

*Primary Examiner* — Si Ming Ku
(74) *Attorney, Agent, or Firm* — Schwegman Lundberg & Woessner, P.A.

(57) ABSTRACT

The present disclosure provides, in certain aspects, unique methods and systems for connecting orthopedic components. In some forms, a male-type projection of a first orthopedic component is securely lodged within a female-type aperture in a second orthopedic component. In one embodiment, the projection, while received through a proximal entryway in the aperture, includes a first longitudinal region with deformed surface elements that provide a first securing zone within the aperture and a second longitudinal region with deformed surface elements that provide a second securing zone within the aperture. The first securing zone is located proximate the distal end of the projection, and the second securing zone is located proximate the proximal entryway of the aperture.

13 Claims, 10 Drawing Sheets

(52) U.S. Cl.
 CPC .......... *A61F 2002/30336* (2013.01); *A61F 2002/30345* (2013.01); *A61F 2002/30349* (2013.01); *A61F 2002/30485* (2013.01); *A61F 2002/30489* (2013.01); *A61F 2002/365* (2013.01); *A61F 2002/4037* (2013.01)

(58) Field of Classification Search
 USPC .......................................... 411/411
 See application file for complete search history.

(56) References Cited

U.S. PATENT DOCUMENTS

| 7,220,283 B2 * | 5/2007 | Terrill | A61F 2/3609 |
| | | | 623/22.44 |
| 2006/0167557 A1 | 7/2006 | Terrill | |

FOREIGN PATENT DOCUMENTS

| FR | 2329249 A1 | 5/1977 |
| WO | WO-2014070616 A1 | 5/2014 |

OTHER PUBLICATIONS

"European Application Serial No. 13786853.5, Response filed Jan. 12, 2016 to Office Action dated Jul. 2, 2015", 11 pgs.

"International Application Serial No. PCT/US2013/066900, International Preliminary Report on Patentability dated May 14, 2015", 11 pgs.

"International Application Serial No. PCT/US2013/066900, International Search Report dated Apr. 7, 2014", 7 pgs.

"International Application Serial No. PCT/US2013/066900, Invitation to Pay Additional Fees and Partial Search Report dated Jan. 21, 2014", 4 pgs.

"International Application Serial No. PCT/US2013/066900, Written Opinion dated Apr. 7, 2014", 9 pgs.

"European Application Serial No. 13786853.5, Response filed Feb. 13, 2017 to Office Action dated Dec. 10, 2016", 9 pgs.

"European Application Serial No. 13786853.5, Communication Pursuant to Article 94(3) EPC dated Aug. 2, 2017", 4 pgs.

"European Application Serial No. 13786853.5, Response filed Dec. 12, 2017 to Communication Pursuant to Article 94(3) EPC dated Aug. 2, 2017", 10 pgs.

* cited by examiner

ORTHOPEDIC CONNECTIONS

CLAIM OF PRIORITY

This application which claims the benefit of U.S. Provisional Patent Application Ser. No. 61/720,064, filed on Oct. 30, 2012, and also claims the benefit of U.S. Provisional Patent Application Ser. No. 61/740,088, filed Dec. 20, 2012, the benefit of priority of each of which is claimed hereby, and each of which are incorporated by reference herein in its entirety.

BACKGROUND

The present disclosure relates generally to medical technology and in some aspects to methods and systems for combining orthopedic components. As further background, mating taper connections can be used for temporarily securing one item to another. One such taper connection is a Morse taper connection. Generally, a Morse taper is defined as a taper connection having a taper surface making an angle of about 2 to 12 degrees relative to the longitudinal axis of the component. Morse taper connections can be made between interpenetrating parts, with, e.g., a first of the parts having a tapered bore, and a second of the parts having a frustoconical shape for securement in the tapered bore of the first part. The tapered bore and the frustoconical shape can have slightly different sizes or taper angles to facilitate securement of the parts via the mating taper connection. To assemble mating taper connections, including Morse taper connections, items having a mating taper structure are interference fit one to the other to cause cointegration or locking of the items. In some cases the cointegration results in material transfer across the zone of contact, i.e., cold welds.

Mating taper connections are used in a vast number of orthopedic devices. For example, modular femoral implants can utilize a Morse taper to secure the proximal body to the distal stem and/or to secure a neck component to a head component. One exemplary modular femoral implant is the modular femoral implant utilized in the ZMR® Hip System produced by Zimmer, Inc. of Warsaw, Ind. In modular femoral implants, the distal stem can include a frustoconical proximal end comprising the male portion of the locking taper, with the longitudinal bore of the proximal body including a mating female taper formed in the distal portion of the longitudinal bore of the proximal body.

SUMMARY

The present disclosure provides, in certain aspects, unique methods andh systems for integrating or connecting orthopedic components. Illustratively, orthopedic components can be connected with an assembly that includes (i) a projection that projects from a first orthopedic component; and (ii) an aperture that is situated in a second orthopedic component. The aperture is adapted to receive at least a portion of the projection for connecting the first orthopedic component to the second orthopedic component. The projection has a general longitudinal axis, and along this axis, the projection includes a truncated generally cone-shaped distal region, a generally cylindrical intermediate region which occurs proximally of the distal region, and a truncated generally cone-shaped proximal region which occurs proximally of the intermediate region. While not necessary to broader aspects of the disclosure, these three regions can occur immediately adjacent one another in succession along the longitudinal axis of the projection. Also, while the cone-shaped regions will generally increase in size in a distal-to-proximal direction, it will be understood that these regions, when viewed from the side, may or may not exhibit a straight-tapered profile. In some instances, a generally cone-shaped region will also feature some form of outward curvature along its length, e.g., by providing a toroidal-like surface profile along the generally cone-shaped region. In some preferred forms, the proximal cone-shaped region will generally be larger than the cone-shaped distal region, e.g., where the maximum diameter of the distal region might approximately equal the minimum diameter of the proximal region. Additionally, the cone-shaped distal region and the cone-shaped proximal region each include one or more deformable surface elements that are deformable upon forcible contact with interior surfaces of the aperture for providing a distal securing zone and a proximal securing zone, respectively, within the aperture when connecting the first orthopedic component to the second orthopedic component. The intermediate region can have any suitable length, e.g., a length of about 2 mm to about 20 mm.

In another aspect, the present disclosure provides an orthopedic assembly that includes a first orthopedic component and a second orthopedic component, e.g., femoral neck and head components. The first orthopedic component includes a projection that comprises a generally tapered longitudinal segment, e.g., one that generally decreases in cross-sectional area in a distal direction. The second orthopedic component includes an aperture, e.g., one that generally increases in cross-sectional area in a proximal direction, for receiving at least a portion of the projection's generally tapered longitudinal segment for connecting the first orthopedic component to the second orthopedic component. The generally tapered longitudinal segment includes (i) a first longitudinal region that has deformable surface elements extending substantially around it; (ii) a second longitudinal region that has deformable surface elements extending substantially around it; and (iii) an intermediate region that is located between the first longitudinal region and the second longitudinal region. The deformable surface elements of the first longitudinal region and the deformable surface elements of the second longitudinal region are deformable upon forcible contact with interior surfaces of the aperture for providing a first securing zone and a second securing zone, respectively, within the aperture when connecting the first orthopedic component to the second orthopedic component, with the intermediate region providing a lesser-securing zone within the aperture relative to the first securing zone and the second securing zone or a non-securing zone within the aperture. The intermediate region can have any suitable length, e.g., a length that is at least as long as one of the first longitudinal region and the second longitudinal region, for example, one, two, three, four, five or more times longer.

In yet another aspect, the present disclosure provides an orthopedic connection that connects a plurality of orthopedic components. This particular orthopedic connection includes (i) a projection that projects from a first orthopedic component; and (ii) an aperture that is situated in a second orthopedic component. The aperture has a proximal entryway through which a distal end of the projection can be received, and at least a portion of the projection is received in the aperture in a fashion that securely connects the first orthopedic component to the second orthopedic component. In particular, the projection, while received in the aperture, includes a first longitudinal region with deformed surface elements that provide a first securing zone within the aperture and a second longitudinal region with deformed surface elements that provide a second securing zone within the aperture. The first securing zone is located proximate the distal end of the projection, and the second securing zone is located proximate the proximal entryway of the aperture. Each of the first and second longitudinal regions can be shaped and configured in a variety of manners including embodiments in which one or both have an overall generally conical or tapered shape. In some aspects, the projection, while received in the aperture, includes an intermediate region that is situated between the first longitudinal region and the second longitudinal region. This intermediate region is essentially non-deformed by walls of the aperture, and can have any suitable length, e.g., a length of at least about 2 mm, 4 mm, 6 mm, 8 mm, 10 mm or more.

In still another embodiment, the present disclosure provides a method for connecting a plurality of orthopedic components. This particular method includes providing a first orthopedic component and a second orthopedic component. A projection projects from the first orthopedic component, and an aperture is situated in the second orthopedic component. The aperture has a proximal entryway through which a distal end of the projection can be received. In still another step, the projection is received in the aperture so as to securely connect the first orthopedic component to the second orthopedic component. This receiving includes deforming surface elements on a first longitudinal region of the projection so as to provide a first securing zone within the aperture and deforming surface elements on a second longitudinal region of the projection so as to provide a second securing zone within the aperture. The first securing zone is located proximate the distal end of the projection, and the second securing zone is located proximate the proximal entryway of the aperture. Additionally or alternatively, deformable surface elements can be located on inner walls of the aperture for contributing to or generating securing zones within the aperture.

In a further aspect, the present disclosure provides a method for connecting a plurality of orthopedic components together. In this particular method, first and second orthopedic components are provided. A projection projects from the first orthopedic component, and an aperture is situated in the second orthopedic component. As part of this method, the projection is received in the aperture so as to securely connect the first orthopedic component to the second orthopedic component. This receiving includes a first longitudinal region of the projection making significant contact with walls of the aperture so as to provide a first securing zone within the aperture and a second longitudinal region of the projection making significant contact with walls of the aperture so as to provide a second securing zone within the aperture. The first securing zone and the second securing zone are separated by an intermediate zone within the aperture in which the projection makes insignificant or no contact with walls of the aperture. In some forms, the intermediate zone is at least 1 mm in length.

In a further aspect, the present disclosure provides a method for connecting a plurality of orthopedic components. This particular method includes providing first and second orthopedic components. A projection projects from the first orthopedic component, and includes (i) a first longitudinal region that has deformable surface elements extending substantially around it; (ii) a second longitudinal region that has deformable surface elements extending substantially around it; and (iii) an intermediate region that is located between the first longitudinal region and the second longitudinal region. An aperture is situated in the second orthopedic component, and as part of the method, the projection is received in the aperture. This includes forcibly contacting the deformable surface elements of the first longitudinal region and the deformable surface elements of the second longitudinal region with interior surfaces of the aperture so as to deform the deformable surface elements of the first longitudinal region and the deformable surface elements of the second longitudinal region to create a first securing zone and a second securing zone, respectively, within the aperture to securely connect the first orthopedic component to the second orthopedic component, with the intermediate region providing a non-securing zone within the aperture or a lesser-securing zone within the aperture relative to the first securing zone and the second securing zone.

In a further aspect, the present disclosure provides a connecting assembly for connecting a plurality of orthopedic components. This particular connecting assembly includes a male-type connecting member that projects from a first orthopedic component and has a general longitudinal axis. The assembly further includes a second orthopedic component. A female-type aperture is situated in the second component for receiving at least a portion of the male-type connecting member for connecting the first orthopedic component to the second orthopedic component. The male-type connecting member includes a distal longitudinal segment and a proximal longitudinal segment. In a single reference plane that includes the general longitudinal axis, the distal longitudinal segment extends in a linear fashion and the proximal longitudinal segment extends in a curvilinear fashion. While the distal longitudinal segment and/or the proximal longitudinal segment may have a generally smooth outer surface, in some embodiments, one or both will optionally include one or more deformable surface features. In a preferred embodiment, a single continuous helical thread extends over at least part of the proximal longitudinal segment and extends over at least part of the distal longitudinal segment. Also, the aperture can have a truncated generally conical shape with a taper angle that is less than a taper angle of the truncated generally cone-shaped distal segment.

In a further aspect, the present disclosure provides a connecting assembly for connecting a plurality of orthopedic components. This particular connecting assembly includes a male-type connecting member that projects from a first orthopedic component and has a general longitudinal axis. The assembly further includes a female-type aperture that is situated in a second orthopedic component for receiving at least a portion of the male-type connecting member for connecting the first orthopedic component to the second orthopedic component. The male-type connecting member includes a threaded or otherwise grooved longitudinal segment, e.g., a single continuous threaded along the longitudinal segment or a plurality of successive, generally circumferential grooves along the longitudinal segment (e.g., extending around the member in a perpendicular or angled fashion with respect to the longitudinal axis of the member), with a distal region and a proximal region. In a single reference plane that includes the general longitudinal axis, the distal region includes a first set of successive thread or groove peaks that extends in a linear fashion and a second set of successive thread or groove peaks that extend in a curvilinear fashion. In a preferred embodiment, the male-type connecting member further includes a non-threaded or non-grooved longitudinal segment that is located distally of the threaded or grooved longitudinal segment.

In a further aspect, the present disclosure provides a connecting assembly for connecting a plurality of orthopedic components. This particular connecting assembly includes a male-type connecting member that projects from a first orthopedic component and has a general longitudinal axis. The assembly further includes a female-type aperture that is situated in a second orthopedic component for receiving at least a portion of the male-type connecting member for connecting the first orthopedic component to the second orthopedic component. The male-type connecting member includes a longitudinal segment that extends in a non-linear fashion in a proximal-distal direction, e.g., approximating the zone of a sphere, or having an outer surface that approximates an outer surface of a torroid or partial-torroid.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
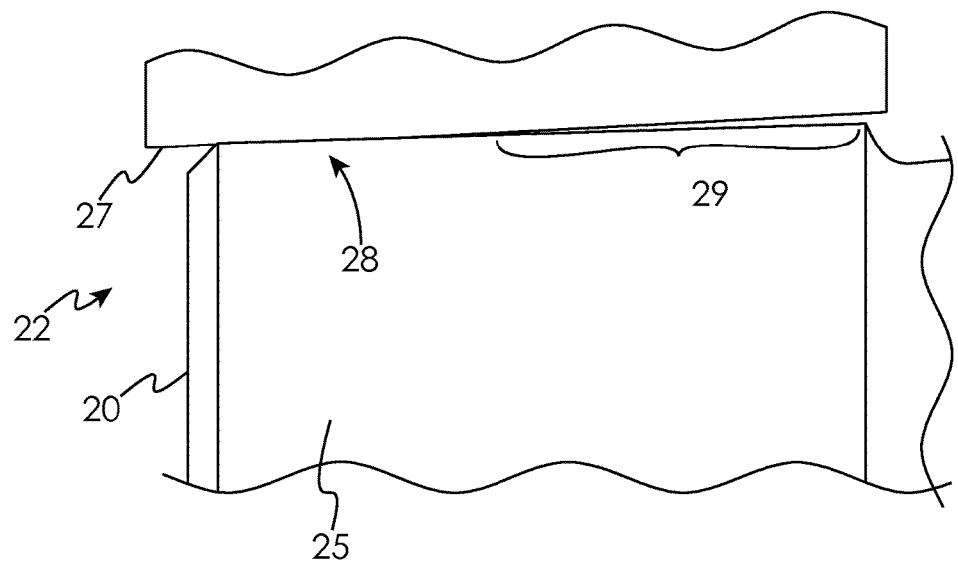
FIG. 1 is a partial, side view of a mating taper connection of the prior art.

FIG. 1 shows a partial, side view of a mating taper connection of the prior art that secures a first component to a second component. In particular, a male member 20 of the first component is received in a tapered, female bore 22 in the second component. Male member 20 includes a distal, frustoconically-shaped segment 25 which has a slightly different taper angle than female bore 22, i.e., a smaller taper angle measured against the central, longitudinal axes of the male-female components which are concentric with one another when secured together. In this regard, sufficiently forcing male member 20 into female bore 22 causes an interference fit between the outer surface of frustoconically-shaped segment 25 and walls 27 of the female bore. This sort of connection includes contact between the two pieces in a distal longitudinal region 28; however, there is no contact between the two pieces in a more proximal longitudinal region 29.

Figure 2:
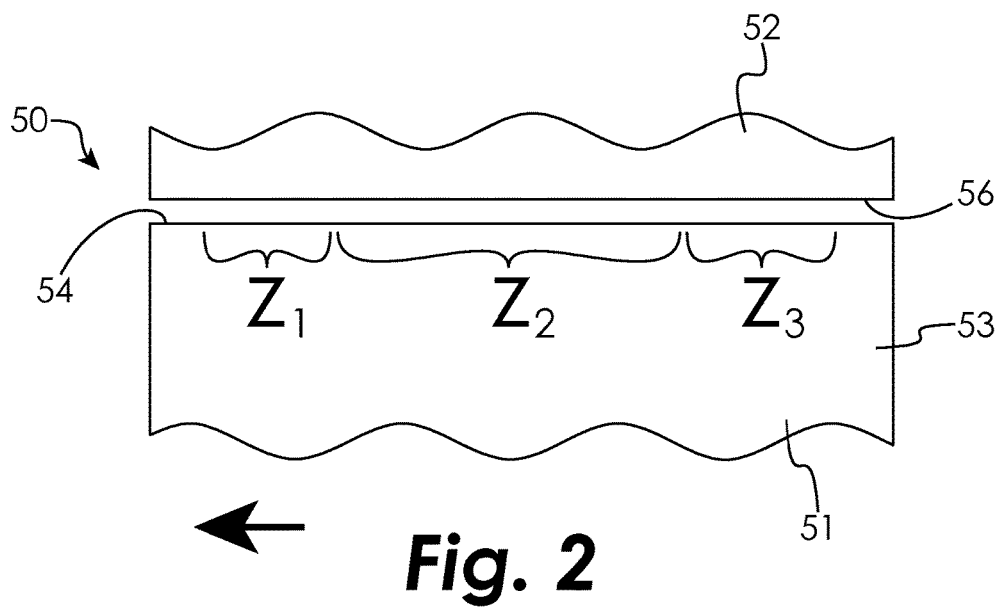
FIG. 2 is a partial, side view of a connection according to one embodiment of the present disclosure.

As disclosed above, in certain aspects, the present disclosure provides unique methods and systems for connecting orthopedic components. With reference now to FIG. 2, shown is a partial, side view of an orthopedic connection 50 according to one embodiment of the present disclosure in which a first implant component 51 is connected to a second implant component 52. In certain aspects of the disclosure, the first implant component is a male-type member 53 which is longitudinally received in a female bore of the second implant component in the direction of the arrow shown. For example, male-type member 53 might be on a femoral neck component, while the female bore might be located in a femoral head or a related head component. Yet, it will be understood that the systems and methods disclosed herein could be utilized in any number of orthopedic applications which includes being utilized in conjunction with various foot, ankle, knee, hip, spine, shoulder, elbow, wrist and hand implants and associated methods. First implant component 51 and/or second implant component 52 can each incorporate or be formed with any suitable biocompatible material including ceramics, synthetic polymeric materials and/or metallic materials such as titanium, a titanium alloy, cobalt chromium, cobalt chromium molybdenum, tantalum, or a tantalum alloy.

Continuing with FIG. 2, in this instance, male-type member 53 includes a side exterior 54, while the female bore includes interior side walls 56. For clarity, the form of contact between the side exterior 54 of the male-type member and the interior side walls 56 of the female bore is not shown in FIG. 2, yet it will be understood that there is significant contact in first longitudinal zone $Z_1$ and third longitudinal zone $Z_3$. In this regard, any of the forms of contact disclosed herein for securing two objects together, or at least helping to secure them together, can occur in these zones. For example, as discussed with respect to certain embodiments disclosed herein, side exterior 54 and/or interior side walls 56 can each incorporate one or more deformable surface features. Such features can become deformed as the male-type member is forcibly received within the female bore of the second implant component so that deformed surface elements eventually reside in longitudinal zone $Z_1$ and longitudinal zone $Z_3$ and thereby facilitate a secure connection between the first implant component 51 and the second implant component 52. In longitudinal zone $Z_2$, there is no contact between the side exterior 54 of the male member and the interior side walls 56 of the female bore, or there is considerably less contact compared to longitudinal zones $Z_1$ and $Z_3$.

Also for clarity, the main surfaces of side exterior 54 and interior side walls 56 are shown as parallel to one another in FIG. 2. While this may occur with respect to certain embodiments disclosed herein, it will be understood that the main opposing surfaces along any of the longitudinal zones $Z_1$ through $Z_3$ can be generally parallel to one another, or they can be non-parallel. For example, the male-type member 53 and the female bore of the second implant component 52 can both have a generally constant taper along their lengths but with slightly different taper angles in a manner that generates deformed surface elements in longitudinal zones $Z_1$ and $Z_3$.

As another illustrative example, a female bore might have an essentially constant taper along its length, while a mateable male-type member might include longitudinal regions with differing degrees of taper and/or differing shapes so that the forcible combination of the male and female pieces generates deformed surface elements in longitudinal zones $Z_1$ and $Z_3$, for example, where a longitudinal region of the male-type member has a generally tapered shape overall but also incorporates another shape (e.g., toroidal) along the surface of the region. As yet another illustrative example, a male-type member might have an essentially constant taper along its length, while a mateable female bore might include longitudinal regions with differing degrees of taper and/or differing shape so that the forcible combination of the male and female pieces generates deformed surface elements in longitudinal zones $Z_1$ and $Z_3$, for example, where a longitudinal region of the female bore has a generally tapered shape overall but also incorporates another shape (e.g., toroidal) along the surface of the region.

Figure 3:
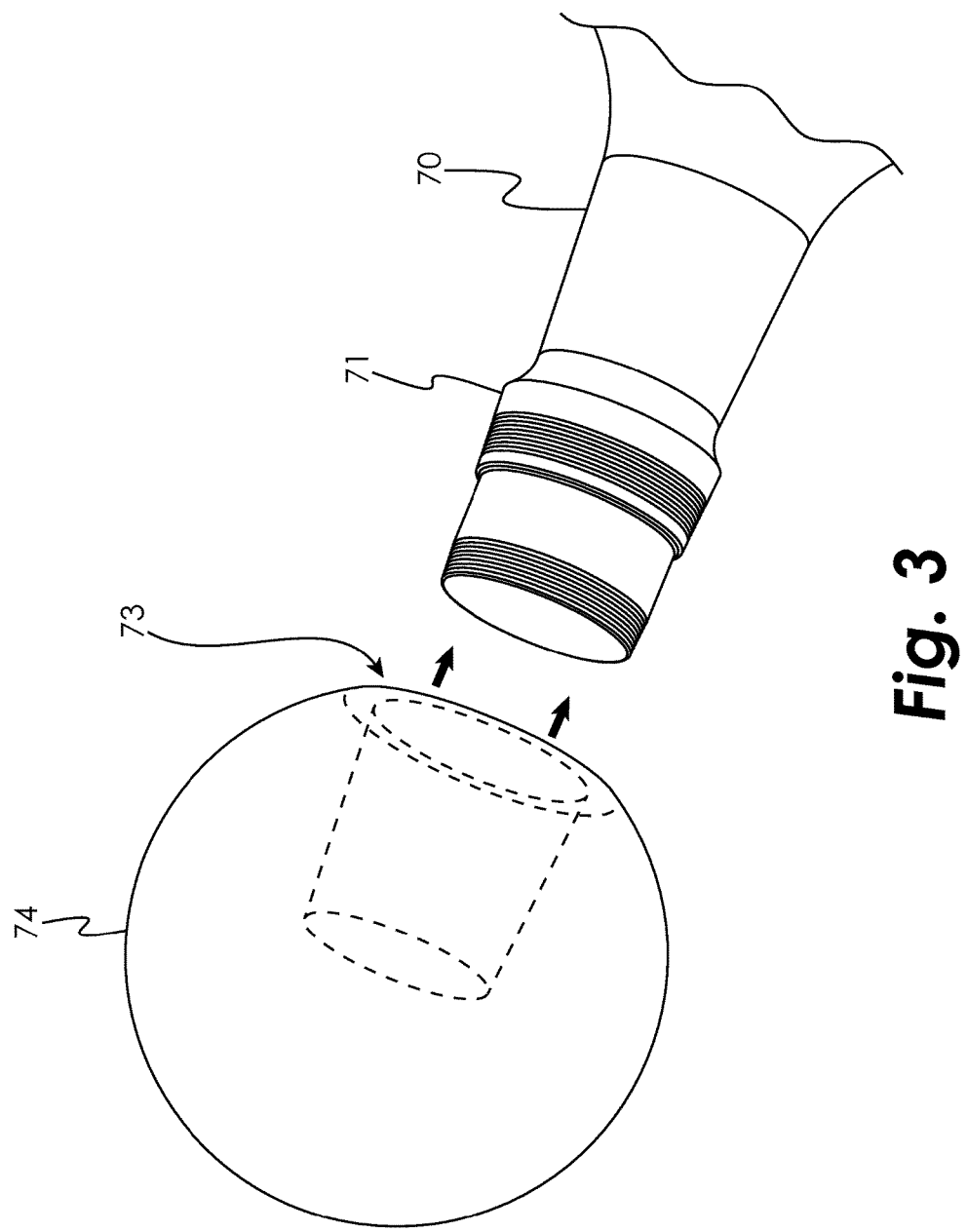
FIG. 3 is a perspective view of femoral neck and head components according to one embodiment of the present disclosure.

With reference now to FIG. 3, shown are components of a modular hip prosthesis according to one embodiment of the present disclosure. In particular, a neck component 70 includes a free end portion 71 which is receivable in a female bore 73 of an illustrative head component 74 for securing the neck component to the head component. Any suitable single- or multiple-piece head or ball component can be utilized in this regard including those incorporating metal, ceramics and/or synthetic polymeric materials. Neck component 70, which projects from a proximal portion of a hip stem (not shown in FIG. 3), may be monolithically formed with the other hip stem portions (e.g., a proximal stem portion, a distal stem portion, etc.), or it may be modularly connectable to these other hip stem portions. Any suitable modular or non-modular hip stem incorporating free end portion 71 may be utilized in this regard. According to an exemplary embodiment of the present disclosure, neck component 71 can be formed with or incorporate a Ti-6Al-4V ELI alloy such as Tivanium® which is available from Zimmer, Inc., of Warsaw, Ind.

Figure 4:
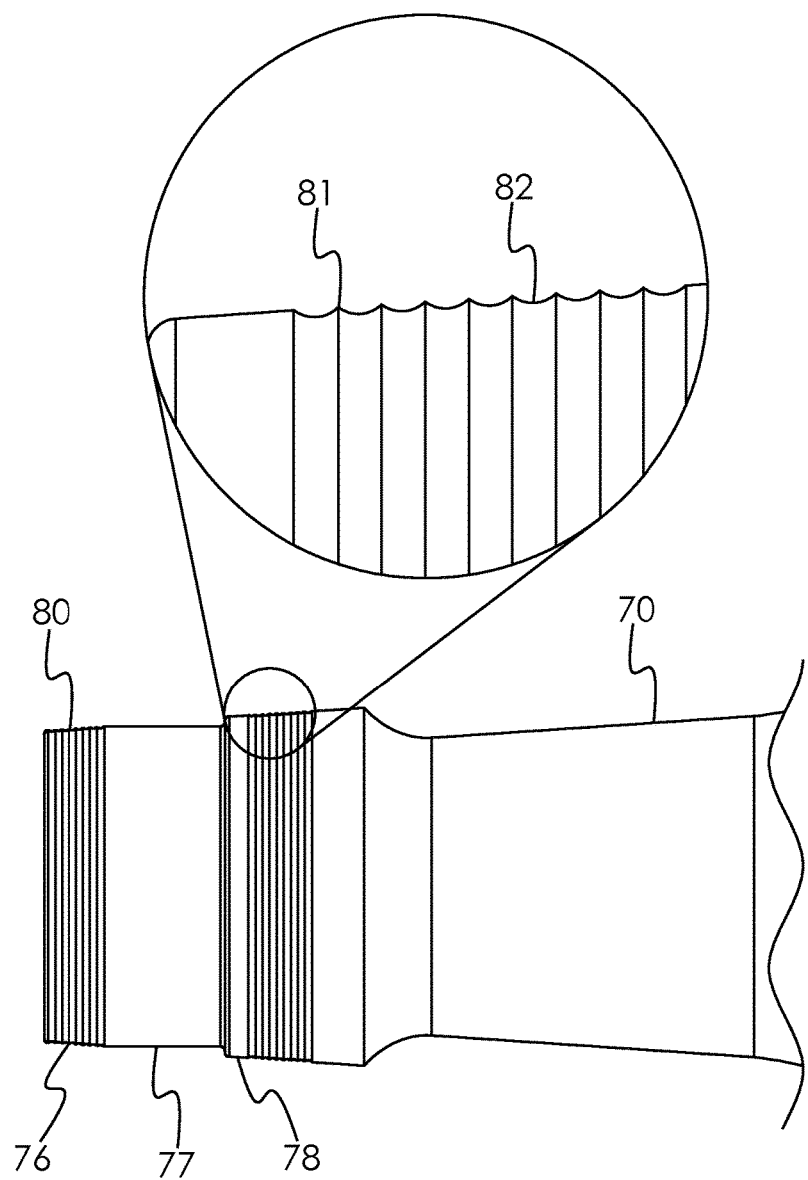
FIG. 4 is a partial, side view of the femoral neck component of FIG. 3.

FIG. 4 is a side view of neck component 70 which shows that free end portion 71 includes a generally frustoconical distal region 76. Proximal of this distal region is a generally cylindrical intermediate region 77, and proximal of this intermediate region is a generally frustoconical proximal region 78. Each of these regions can have any suitable length along the free end portion 71. Distal region 76 and proximal region 78 each include a plurality of deformable surface elements which in this particular instance are a series of circumferential and longitudinally successive surface ridges 80 extending along a significant portion of each frustoconically-shaped region. Intermediate region 77 is void of such ridges although ridges can be present there in some embodiments. While not necessary to broader aspects of the disclosure, it is notable that the deformable surface elements extend along substantially the entire length of frustoconical distal region 76 while extending only partially along frustoconical proximal region 78. Either arrangement is suitable for either frustoconical region. Also notable is that the intermediate region 77 can have substantial length. In this specific illustrative embodiment, the intermediate region happens to be cylindrical and is approximately twice as long as each swath or grouping of deformable surface elements, i.e., those on distal region 76 and proximal region 78.

In this regard, it will be understood that any grouping of deformable surface elements (e.g., those occurring on distal region 76 or proximal region 78 in FIG. 4) or any grouping of deformed surface elements (e.g., those occurring in longitudinal zone $Z_1$ or longitudinal zone $Z_3$ in FIG. 2) can have any suitable length along an orthopedic component (e.g., a male-type member or walls of a female bore). For example, a grouping of deformed or deformable surface elements along an orthopedic component can be from about 1 mm to about 50 mm or more in length, for example, from about 2 mm to about 40 mm in length, or from about 3 mm to about 15 mm in length, or at least any one of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm or 20 mm in length, but typically less than about 80 mm in length. Also, within a single orthopedic component, any two such groupings may or may not have the same length along the component, and there can be more than two groupings of deformed or deformable surface elements along an orthopedic component separated by lesser- or non-securing intermediate zones or regions. With regard to lesser- or non-securing zones or regions (e.g., longitudinal zone $Z_2$ in FIG. 2 or intermediate region 77 in FIG. 4), they too can have any suitable length along an orthopedic component, and this length may be the same, lesser or greater than any adjacent grouping of deformed or deformable surface feature. For example, such zones or regions can be from about 1 mm to about 60 mm or more in length, for example, from about 2 mm to about 40 mm in length, or from about 8 mm to about 25 mm in length, or at least any one of 1 mm, 2 mm, 4 mm, 6 mm, 8 mm, 10 mm, 12 mm, 14 mm, 16 mm, 18 mm, 20 mm, 22 mm, 24 mm, 26 mm, 28 mm, 30 mm, 32 mm, 34 mm, 36 mm, 38 mm or 40 mm in length, but typically less than about 120 mm in length, and these lengths can work in conjunction with any suitable length(s) of adjacent groupings of deformed or deformable surface features. Also, while not necessary to broader aspects of the disclosure, according to some embodiments, a lesser- or non-securing zone or region along an orthopedic component will have a greater length than a grouping of adjacent deformed or deformable surface features, e.g., being from about 1.5 times to about 20 times or more greater, e.g., at least any one of 2, 3, 4, 5, 6, 7, 8, 9 or 10 times greater.

Continuing with FIG. 4, it includes an enlarged, side view of the deformable surface elements located in proximal region 78. The elements are comprised of a series of longitudinally successive peaks 81 and valleys 82 which act to provide a corresponding series of circumferential grooves extending around the proximal region 78. When viewed from the side, the valleys 82 appear generally curved. While the shape, size and other characteristics of the peaks 81 and valleys 82 shown in FIG. 4 will certainly be useful in some contexts, they are merely illustrative of one embodiment of the disclosure. When an element has deformable surface elements with peaks and valleys, features such as the number of grooves in a region, the height and width of the peaks 81, the depth and width of the valleys 82, the longitudinal distance between successive peaks 81 or valleys 82, the shape of the peaks 81 or valleys 82, and/or other characteristics can be adjusted as desired for a particular orthopedic application. For example, when viewed from the side, a deformable surface element or any associated feature such as a peak or a valley can exhibit a variety of rectilinear and/or curvilinear shapes. In this regard, a variety of circumferential or partially circumferential surface elements are contemplated including several different types of rings, corrugations, bands, threading, helical structures, annular elements and ridges. Such elements can be formed in any suitable manner including by cutting away, grinding away or otherwise removing material from an initial work piece to provide one or more deformable surface elements, or by welding, adhering or otherwise adding material to an existing piece to provide one or more deformable surface elements, or by casting or otherwise initially forming a component (e.g., using an additive manufacturing type of process) to have one or more deformable surface elements.

Additionally, continuing with FIG. 4, while not necessary to broader aspects of the disclosure, it is notable that these particular grooves run straight, are parallel to one another, and are perpendicular to the central longitudinal axis of the proximal region 78. In other embodiments, such grooves or other elongated or directional surface elements can be non-straight and/or can run at an angle or parallel to the longitudinal axis of the underlying orthopedic element (e.g., where a groove, surface ridge, etc. is wavy or oscillates along its length). In some aspects, one or more helical, serpentine-like, or threaded surface elements are utilized.

Figure 5A:
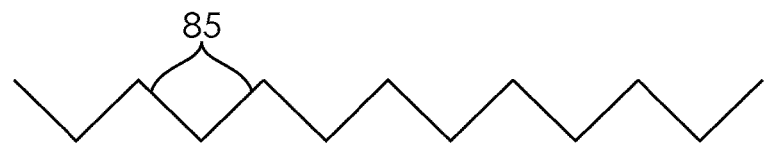
FIG. 5a is a side view of deformable surface elements according to one embodiment of the present disclosure.
Figure 5B:
FIG. 5b is a side view of deformable surface elements according to another embodiment of the present disclosure.
Figure 5C:
FIG. 5c is a side view of deformable surface elements according to yet another embodiment of the present disclosure.

Turning now to FIGS. 5A through 5C, they show partial, side views of just some of the alternative surface profiles contemplated for providing circumferential surface grooves or ridges along distal region 76 or proximal region 78 or along any other surface or region disclosed herein that might provide circumferential or partially circumferential deformable surface features. Illustratively, the longitudinally successive elements in FIG. 5A, when viewed from the side, have side walls 85 that run generally at a 45 degree angle relative to the central, longitudinal axis of the underlying orthopedic element. The surface features in FIG. 5B, when viewed from the side, include generally rectangular surface projections 86 which are longitudinally spaced from one another along the underlying orthopedic element. The surface features in FIG. 5C, when viewed from the side, include curvilinear shapes 87 which are longitudinally spaced from one another along the underlying orthopedic element.

Referring again to FIG. 4, in this specific illustrative example, the general angle at which the frustoconical regions are inclined relative to the central longitudinal axis of the free end portion can be measured, for example, by drawing a line through successive peaks 81 or through the bottom-most points of successive valleys 82 of the deformable surface elements. While not necessary to broader aspects of the disclosure, the general angle at which frustoconical distal region 76 is inclined relative to the central longitudinal axis of the free end portion 71 is essentially the same as the general angle at which frustoconical proximal region 78 is inclined relative to the central longitudinal axis of the free end portion 71. In some forms, these angles will be different, for example, where the distal region is angled to a lesser degree relative to the central longitudinal axis of the free end portion 71 than the proximal region, or vice versa. Additionally, while it certainly will be advantageous in certain embodiments for the lines drawn through successive peaks or valleys to be straight as in free end portion 71, such lines can have curved or other non-straight profiles as well, for example, when viewed from the side as in FIG. 4. Illustratively, a longitudinal region can have on overall generally tapered shape but additionally incorporate an exterior surface profile resembling the outer exterior surface of a toroid. In this regard, for example, a generally frustoconically-shaped region like those shown in FIG. 4 instead could be configured so that a line drawn through successive peaks 81 or valleys 82, when viewed from the side, produces a generally convex or other regular or irregular outwardly-curved shape.

Referring again to FIG. 3, in use, free end portion 71 can be received in female bore 73 of head component 74 such that several of the surface ridges 80 are deformed upon forcible contact with interior walls or surfaces of the female bore 73. With sufficient force and contact, a distal securing zone can be generated in relation to one or more deformed surface ridges of distal frustoconical region 76, and a proximal securing zone can be generated in relation to one or more deformed surface ridges of proximal frustoconical region 78 to facilitate a secure connection between the neck and the head components. Like the free end portion 71, the female bore 73 can be shaped and configured in a variety of manners to influence things such as the type, amount, and timing of contact between the deformable surface features and inner surfaces of the bore. For example, the free end portion 71 and female bore 73 can be cooperatively shaped and sized so that a first deformable surface ridge of the distal frustoconical region 76 contacts an inner wall of the female bore before, after, or as a first deformable surface ridge of the proximal frustoconical region 78 contacts an inner wall of the female bore. In this regard, any region of a male-type member and any region of a mating female bore or passage such as those shown in FIG. 3 can incorporate any suitable three-dimensional rectilinear and/or curvilinear shape. These include but are not limited to full and partial forms of wedges, tapered bodies, toroids, conoids, catenoids, tetrahedrons, cubes, parallelepipeds, prisms, pyramids, cones, cylinders, and combinations of the same.

Figure 6:
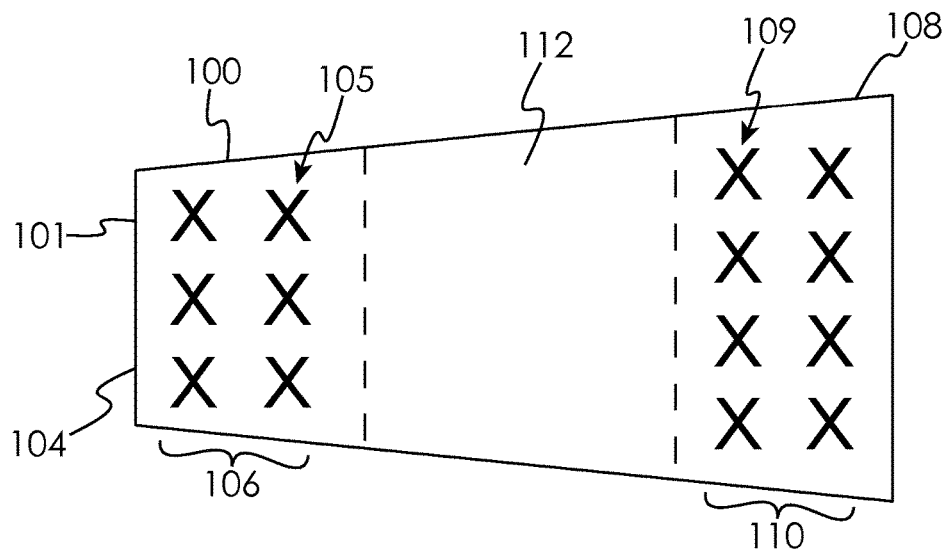
FIG. 6 shows a side view of an orthopedic component according to one embodiment of the present disclosure.

FIG. 6 shows a side view of a generally cone-shaped member 100 according to one aspect of the present disclosure which, for example, can be a projection with a free distal end 101 projecting from a first orthopedic component such as a femoral or humeral neck component. Member 100 has been lodged within a generally conical mating bore of a second orthopedic component (not shown) such as a head or ball component, and in this condition, the member 100 includes a first longitudinal region 104 with deformed surface elements 105 contacting inner walls of the bore to provide a first securing zone 106 within the bore, and a second longitudinal region 108 with deformed surface elements 109 contacting inner walls of the bore to provide a second securing zone 110 within the bore. For clarity, the letters "X" have been used to indicate one or more deformed surface features in each of first longitudinal region 104 and second longitudinal region 108. It will be understood that such deformed surface features can include any of those disclosed herein including circumferential or partially circumferential surface ridges that have been forcibly deformed. In some embodiments, one or more regions of an orthopedic element such as regions 104 or 108 will include more discrete-looking deformable surface features such as but not limited to bumps, bulges, lumps, knobs, protuberances, dimples, depressions, dents, and/or other more discrete-looking projections or indentations. Such features can be arranged in regular or irregular patterns along a region.

Continuing with FIG. 6, it is notable that the first securing zone 106 is located near the distal end of the projection, while the second securing zone is located well proximal of the first securing zone. A lesser or non-securing zone 112 separates the first securing zone 106 from the second securing zone 110. The lesser or non-securing zone 112 can extend along a significant length of the member 100, for example, exceeding the length of the first securing zone 106 and/or the second securing zone 110 as shown. In some instances, the second securing zone will be located proximate a proximal entryway of the bore.

Figure 7:
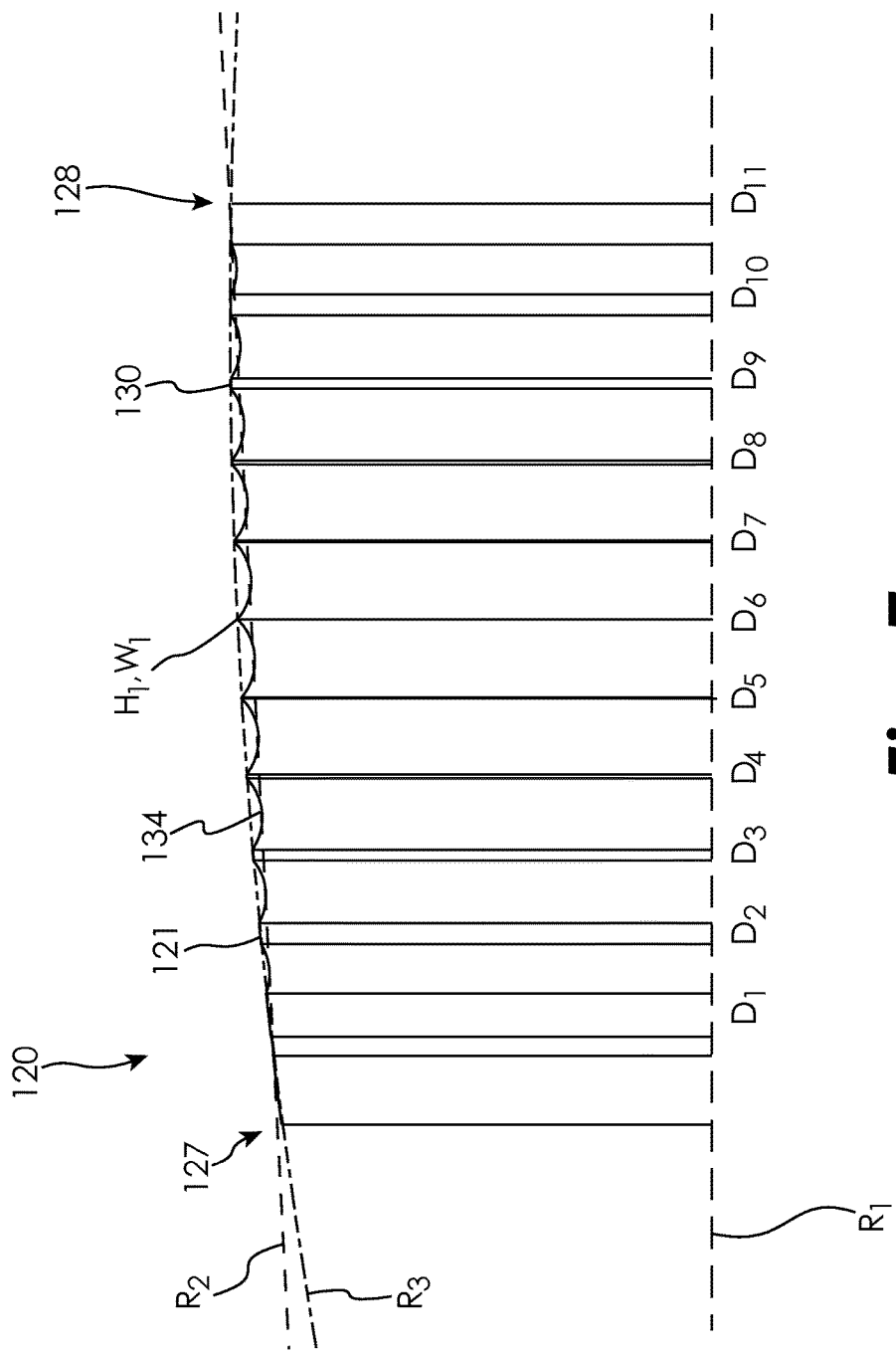
FIG. 7 shows a partial, side view of an orthopedic component according to one embodiment of the present disclosure.

As discussed above, in some embodiments, a longitudinal section along a male-type member or a longitudinal region within a receiving-type female bore will generally taper off along its length but will also incorporate a curved or other non-straight longitudinal surface profile along this length, i.e., when viewed from the side. Such longitudinal sections may or may not incorporate one or more deformable surface features (e.g., a helical or helical-like thread) as discussed elsewhere herein. FIG. 7 is a partial, side view of one such longitudinal section 120 that also happens to incorporate a series of circumferential and longitudinally successive deformable surface ridges 121 that generally run straight, are parallel to one another, and are perpendicular to, generally perpendicular to or somewhat angled to the central longitudinal axis of the neck. When angled (e.g., forming part of one or more helical threads along a longitudinal section), such ridges or other deformable surface features can be angled to any suitable degree relative to the central longitudinal axis of the neck. These deformable elements are marked $D_1$-$D_{11}$ in FIG. 7. Of course, more or fewer of these or other deformable surface features could be utilized. Such a longitudinal section could be incorporated into a male-type member or form part of a wall within a female bore. In this regard, the set of deformable surface ridges $D_1$-$D_{11}$ shown in FIG. 7 could be substituted for either or both groups of deformable surface ridges incorporated into the neck component 70 shown in FIG. 4. Thus, referring to such a modified version of FIG. 4, each of the longitudinal neck portions 76 and 78, in addition to generally tapering off toward the distal end of the neck and providing a set of deformable surface ridges, could also exhibit some type of radially-outward curvature along its length, for example, as will now be explained with regard to FIG. 7.

When longitudinal section 120 is viewed from the side as in FIG. 7, a first dashed reference line $R_1$ represents a line running parallel to the central longitudinal axis of the neck, whereas a second dashed reference line $R_2$ (also a straight line like reference line $R_1$) is angled to some degree (e.g., in the range of about 2-12 degrees, or about 1-6 degrees) relative to the central longitudinal axis of the neck. This angled could be termed a half angle. In this particular illustrative example, the outer surface of longitudinal section 120 includes a distal reference point 127 and a proximal reference point 128 which are both located along the second dashed reference line $R_2$. However, between these two points, the peaks 130 of the deformable surface ridges 121 are located along an outwardly-curved, third dashed reference line $R_3$ which travels above the second dashed reference line $R_2$ in a convex-like manner when viewed from the side, and in this regard, it can be said that the peaks have a radial extent that is greater than that of the longitudinal section's outer surface at distal reference point 127 and proximal reference point 128. In particular, starting at or near distal reference point 127 and moving in a proximal direction toward proximal reference point 128, the height of the peaks gradually increases, that is, moving from the peak at ridge $D_1$ to a maximum peak height $H_1$ which can be associated with one or more ridges including ridge $D_6$, and then gradually decreases until reaching a point at or near proximal reference point 128. In this particular instance, when viewed from the side, the maximum height occurs at a single ridge which is ridge $D_6$ although a maximum height could be shared by two or more such ridges in other embodiments. While curved reference line $R_3$ in this particular illustrative embodiment has a generally constant radius, this is not required. Many other designs are contemplated in which such a reference line marking successive peaks of deformable surface elements could exhibit any suitable shape including those with rectilinear and/or curvilinear features. Also, when a curved reference line of this sort has a generally constant radius, this radius can be larger or smaller than that shown in FIG. 7.

Referring still to FIG. 7, it is notable that starting at or near distal reference point 127 and moving in a proximal direction toward proximal reference point 128, the width of the peaks gradually decreases, that is, moving from the peak at ridge $D_1$ to a minimum peak width $W_1$ which can be associated with one or more ridges including ridge $D_6$. As in FIG. 7, this minimum peak width might occur at the peak(s) that have the maximum peak height $H_1$ although this is not required. Then, from this minimum peak width, the width of the peaks gradually increases until reaching a point at or near proximal reference point 128. Coinciding with these changes in peak width are corresponding changes in the width of the valleys 134 situated between successive peaks. In particular, starting at or near distal reference point 127 and moving in a proximal direction toward proximal reference point 128, the width of the valleys 134 gradually increases to a maximum width which can be associated with one or more valleys.

A set of deformable surface ridges 121 having the differential peak and valley attributes set forth in FIG. 7 can be formed in any suitable manner including by cutting away, grinding away or otherwise removing material from an initial work piece to provide one or more deformable surface elements, or by welding, adhering or otherwise adding material to an existing piece to provide one or more deformable surface elements, or by casting or otherwise initially forming a component (e.g., using an additive manufacturing process) to have one or more deformable surface elements. In one preferred embodiment, an initial neck piece includes a longitudinal section with a solid outer surface profile generally matching that of the curved reference line $R_3$, e.g., where the longitudinal section generally tapers off along its length but also incorporates a curved or other non-straight longitudinal surface profile along this length, i.e., when viewed from the side. Thereafter, this initial work piece is cut or grinded away with a groove-cutting tool (e.g., a threading tool) that cuts the grooves or valleys perpendicular to, generally perpendicular to or somewhat angled to the central longitudinal axis of the neck but that is longitudinally tapered generally in line with the second dashed reference line $R_2$. It should be understood that within the context of having a longitudinal section that generally tapers off along its length but also incorporates a curved or other non-straight longitudinal surface profile along this length, i.e., when viewed from the side, the dimensions and number of deformable surface elements can be varied as desired to suit a particular orthopedic connection application. Thus, just to give one example, it would be possible to have a longitudinal section where, starting at or near distal reference point 127 and moving in a proximal direction toward proximal reference point 128, the height of the peaks gradually increases to a maximum height $H_1$ which can be associated with one or more peaks, and then gradually decreases until reaching a point at or near proximal reference point 128, but where the width of the peaks and valleys might remain generally constant throughout this section.

Figure 8:
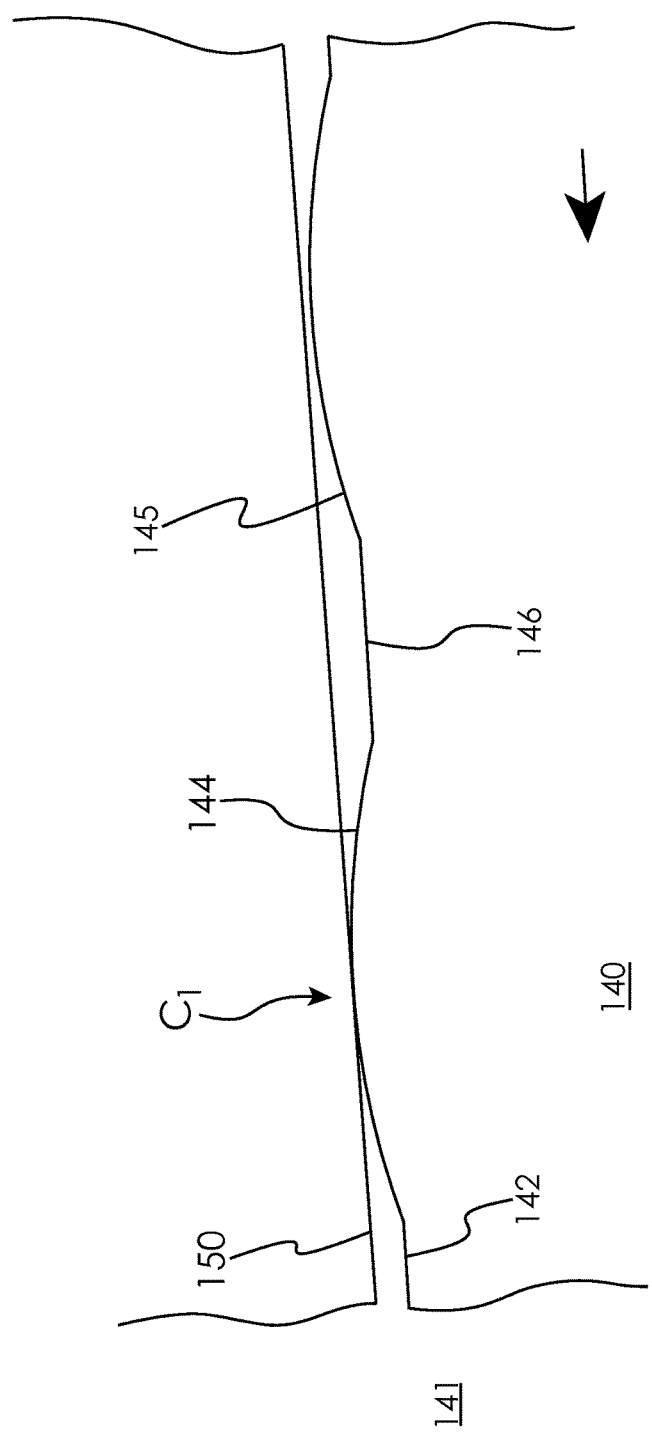
FIG. 8 is a partial, side view of a connection being made according to one embodiment of the present disclosure.

Turning now to FIG. 8, shown is a partial, side view of a connection being made according to one embodiment of the present disclosure. In particular, in the direction of the arrow shown, a neck component 140 is being forcibly received in a female bore 141. Neck component 140, in addition to generally tapering off in a distal direction, incorporates along its outer surface 142 a distal longitudinal section 144 and a proximal longitudinal section 145 which are both identical to the longitudinal section 120 shown in FIG. 7;

however, in the FIG. 8 drawing, the deformable surface ridges have been omitted for the sake of clarity for the following discussion. In this regard, it will be understood that the outwardly-curved surfaces of longitudinal sections 144 and 145 correspond to the curved reference line $R_3$ in FIG. 7 so as to mark the successive peaks of the deformable surface elements $D_1$-$D_{11}$ in each longitudinal section. Additionally, it should be noted that the heights of the convexly-shaped longitudinal sections have been exaggerated upward for illustrative purposes. As disclosed elsewhere herein, these types of outwardly-curved and other uniquely shaped longitudinal sections like distal longitudinal section 144 and/or the proximal longitudinal section 145 can be provided without deformable surface features (e.g., threads, grooves, bumps, etc.) and instead can have generally smooth outer surfaces as they appear in FIG. 8.

Continuing with FIG. 8, when viewed from the side, the outer surface 142 of the neck component also includes non-curved portions which include those indicated at regions 142 and 146. These regions of the outer surface are tapered to a degree relative to the central longitudinal axis of the neck. While not necessary to broader aspects of the disclosure, notably, the starting and ending points of the outwardly-curved distal and proximal longitudinal sections 144 and 145 occur along this line of taper. An interior wall 150 of the female bore is also tapered relative to the central longitudinal axis of the neck but with a slightly different taper angle (i.e., greater in this case) than regions 142 and 146 of the neck component.

In making an orthopedic connection, the shape and orientation of the deformable surface ridges along the distal and proximal longitudinal sections 144 and 145 relative to the taper angle of interior wall 150 are such that, as neck component 140 is being forcibly received in female bore 141, the deformable surface ridges along distal longitudinal section 144 will contact interior wall 150 before those of proximal longitudinal section 145 as shown in FIG. 8. Specifically, referring to FIG. 7 for a view of the shape and orientation of the deformable surface ridges $D_1$-$D_{11}$ along distal longitudinal section 144, as the neck component advances, an initial contact between the neck component and the wall of the female bore (generally shown happening at $C_1$ in FIG. 8) will occur with respect to deformable surface ridge $D_6$ which is the highest and narrowest ridge. The materials involved are such that this contact will partially crush or otherwise deform ridge $D_6$ as the neck component and the interior wall of the female bore are forced longitudinally along and against one another. In this particular illustrative embodiment, as neck component 140 further enters female bore 141, a subsequent contact between the neck component and the wall of the female bore will occur at deformable surface ridge $D_5$ of distal longitudinal section 144. Ridge deformation will continue in this direction, i.e., moving toward ridge $D_1$, although, depending on the particular design characteristics of the male-female components, ridges $D_1$-$D_5$ may never be contacted or deformed in making an orthopedic connection. Also, depending on the particular design characteristics of the male-female components, as ridge $D_6$ is further crushed with the continued advancement of the neck, ridge deformation can start to occur in the opposite direction, i.e., toward ridge $D_{11}$, although, depending on the particular design characteristics of the male-female components, ridges $D_7$-$D_{11}$ may never be contacted or deformed in making an orthopedic connection. This should make it clear that by adjusting things such as the shape, size, and orientation of the deformable surface ridges along the distal and proximal longitudinal sections 144 and 145 and the shape of the female bore, outcomes such as the type, amount and timing of contact between any of the deformable surface ridges along any longitudinal section can be manipulated as desired to suit a particular orthopedic application.

Referring again to FIG. 8, these particular components are designed such that only after one or more of the deformable surface ridges of distal longitudinal section 144 have contacted interior wall 150, an initial contact between proximal longitudinal section 145 and bore wall 150 will occur at that section's deformable surface ridge $D_6$ which is the highest and narrowest ridge of proximal section 145. Then, as above with regard to distal section 144, as neck component 140 further enters female bore 141, subsequent ridge-deforming contacts can occur in a distal and/or proximal direction until a suitable connection is made. In this regard, with sufficient force and contact, a distal securing zone can be generated in relation to one or more deformed surface ridges of distal longitudinal section 144, and a proximal securing zone can be generated in relation to one or more deformed surface ridges of proximal longitudinal section 145 to facilitate a secure connection between the neck and the head components. Once a suitable connection has been made such that relative movement between the neck component and the wall of the female bore has essentially ceased, a no-contact zone of significant length will occur at region 146 and can include, for example, leading and trailing portions of the distal and proximal longitudinal sections 144 and 145 that do not contact the wall of the female bore when the connection is complete. Also, it will be understood that like the neck component 140, the female bore 141 can be shaped and configured in a variety of manners as discussed elsewhere herein to influence things such as the type, amount, and timing of contact between the deformable surface ridges and inner surfaces of the bore. For example, the neck component 140 and female bore 141 can be cooperatively shaped and sized so that a first deformable surface ridge or other deformable surface feature of the distal longitudinal section 144 contacts an inner wall of the female bore before, after, or as a first deformable surface ridge or other deformable surface feature of the proximal longitudinal section 145 contacts an inner wall of the female bore.

Figure 9:
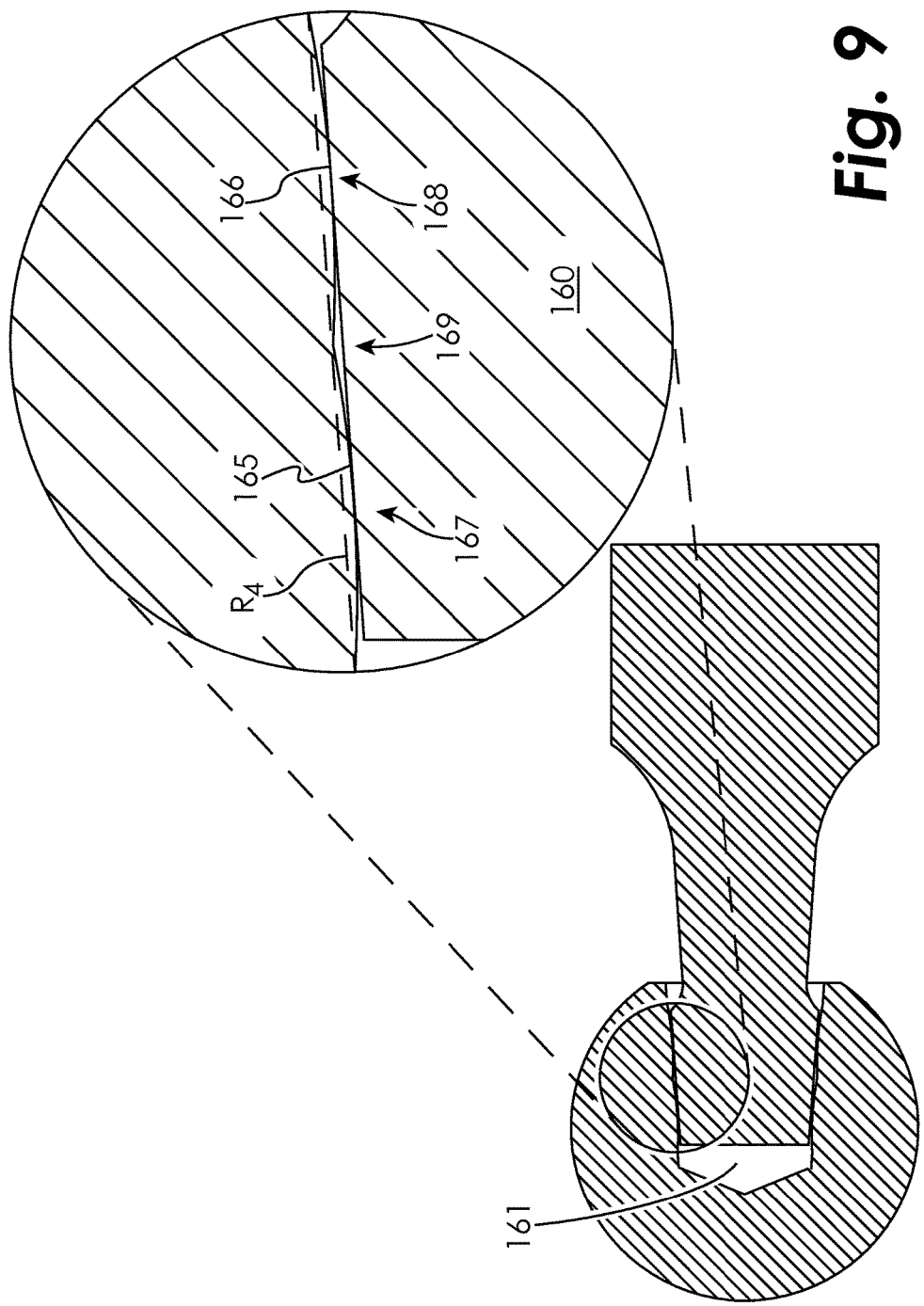
FIG. 9 shows a side view of femoral neck and head components according to one embodiment of the present disclosure.

Turning now to FIG. 9, shown is a side view of a neck component with a male-type member 160 received in a female bore 161 of a head component. Notably, as better seen in the enlarged view, the female bore generally tapers off along its length according to a dashed reference line $R_4$ which is angled to some degree relative to the central longitudinal axis of the bore. However, when viewed form the side, the inner wall of the bore also bows inwardly, i.e., toward the central longitudinal axis of the bore, along a distal longitudinal region 165 and a proximal longitudinal region 166. This sort of bowing gradually narrows the bore in these regions, i.e., as would be compared to a straight-taper bore formed along reference line $R_4$. The male-type member 160 is tapered in a generally straight manner, and the angle of taper may or may not be the same as that of reference line $R_4$. In this particular illustrative example, male-type member 160 has a slightly smaller taper angle than reference line $R_4$ relative to the central longitudinal axis of the bore.

Continuing with FIG. 9, there is significant contact between the two pieces in a distal securing zone 167 and a proximal securing zone 168, while there is no contact in an intermediate zone 169 which includes a location in which the bowed-wall regions of the bore come together along reference line $R_4$. In addition to the above-described features, it will be understood that any of the enhancements disclosed herein for helping to secure the pieces together, can occur in distal securing zone 167 and proximal securing zone 168. For example, as discussed with respect to certain embodiments disclosed herein, the male-type member and/or the walls of the female bore can each incorporate one or more deformable surface features that participate in the significant contact between the two pieces in the securing zones. As one illustrative example, the bowed walls of the female bore may be without deformable surface features, while the male-type member might incorporate such features in regions associated with distal securing zone 167 and proximal securing zone 168. Illustratively, the male-type member 160 can incorporate any number of generally circumferential and longitudinally successive surface features like ridges 80 shown in FIG. 4, for example, where the general angle at which the male-type member would be inclined relative to its central longitudinal axis would be measured by drawing a line through successive peaks or through the bottom-most points of successive valleys of the deformable surface ridges.

Figure 10:
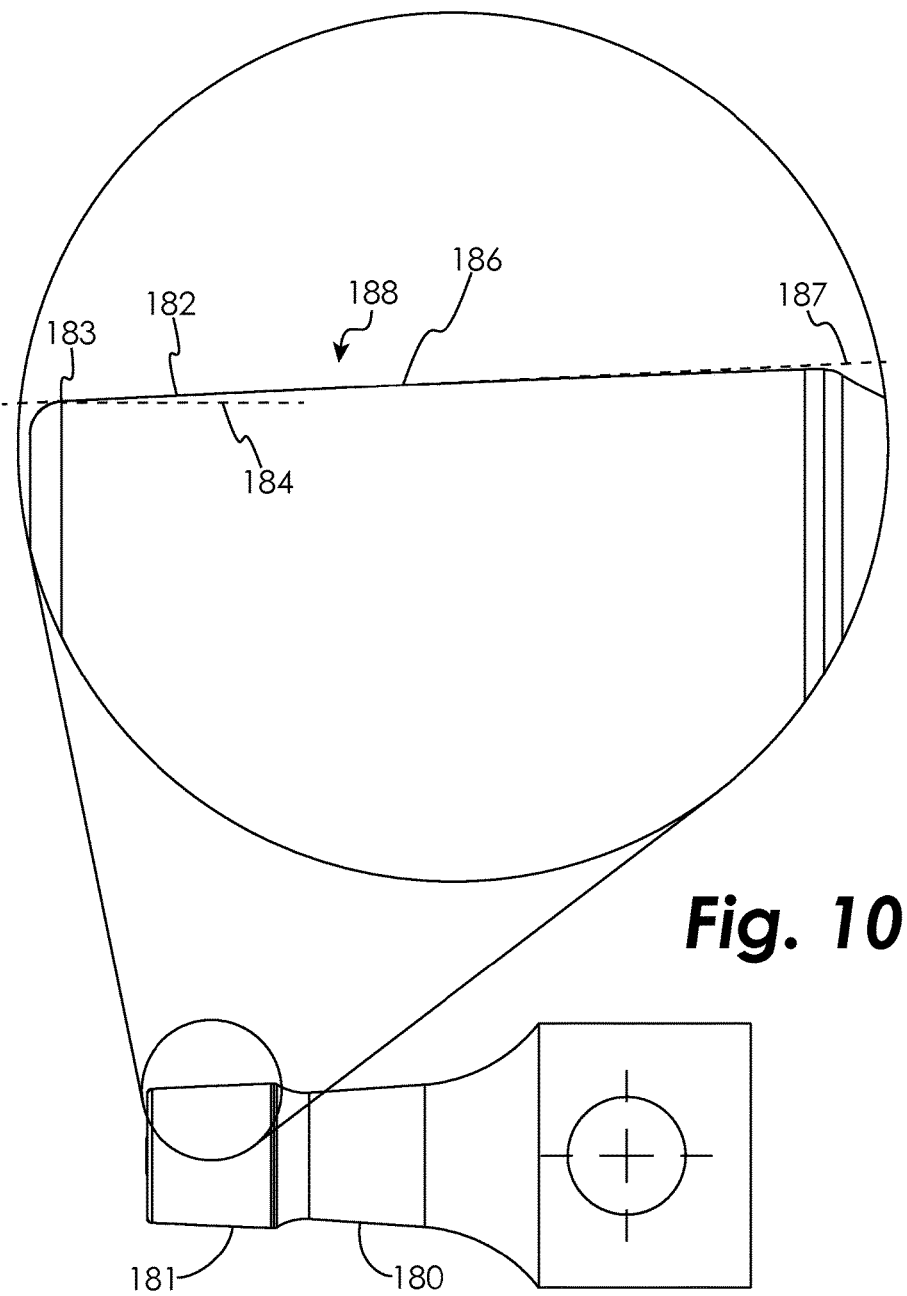
FIG. 10 is a partial, side view of a femoral neck component according to one embodiment of the present disclosure.

As discussed above, in some embodiments, a longitudinal section along a male-type member or a longitudinal region within a receiving-type female bore will incorporate a curved or other non-straight longitudinal surface profile along this length, e.g., when viewed from the side or when viewed in a single reference plane that includes the central longitudinal axis of the member or bore. FIG. 10 is a side view of a neck component 180 according to one embodiment of the present disclosure. Neck component 180 includes a free end portion 181 which can be received in a female bore of a head component for securing the neck component to the head component. Free end portion 181 includes a generally frustoconical distal region 182 that itself has a distal-most location 183. While not necessary, the free end portion also includes a radiused edge distal of the distal-most location 183. When viewed from the side as in FIG. 10, a first dashed reference line 184 represents a line running parallel to the central longitudinal axis of the neck, and it can be seen that distal region 182 has a straight taper (e.g., in the range of about 1-6 degrees, or about 2-3.5 degrees) relative to the central longitudinal axis of the neck.

Continuing with FIG. 10, a proximal region 186 with an outer profile approximating the zone of a sphere or outer surfaces of a torus (e.g., having any suitable radius such as a constant radius in the range of about 100-1,000 mm, or about 200-800 mm, or about 300-700 mm, or about 400-600 mm which may be particularly suitable for some femoral neck embodiments) is located proximally of distal region 182. As discussed elsewhere herein, such a longitudinal region can have any suitable profile when viewed from the side, e.g., including one or more curvilinear sections with a constant or varying radius. A second dashed reference line 187 is shown extending from the distal region 182 to highlight the difference in side profiles between the distal region 182 and proximal region 186 (e.g., linear versus non-linear in this view). Each of these regions can have any suitable length along the free end portion 181, and distal region 182 and proximal region 186 may or may not directly adjoin one another. In this particular embodiment, they are in fact adjoining, and while not necessary to broader aspects of the disclosure, the circular profile of the proximal region 186 is made to be tangent or nearly tangent to the straight taper of the distal region 182 at location 188. In this regard, the second dashed reference line 187 shows how the size and placement of this particular curved shape reduces the overall width of the free end portion 181 in its more proximal regions, i.e., compared to a free end portion actually extending along reference line 187. Additionally, as discussed elsewhere herein, while not necessary to broader aspects of the disclosure, distal region 182 and/or proximal region 186 can each incorporate one or more deformable surface features such as a plurality of successive, generally circumferential grooves along a region (e.g., extending around distal region 182 and/or proximal region 186 in a perpendicular or angled fashion with respect to the longitudinal axis of the free end portion) or a single continuous helical or helical-like thread.

Figure 11:
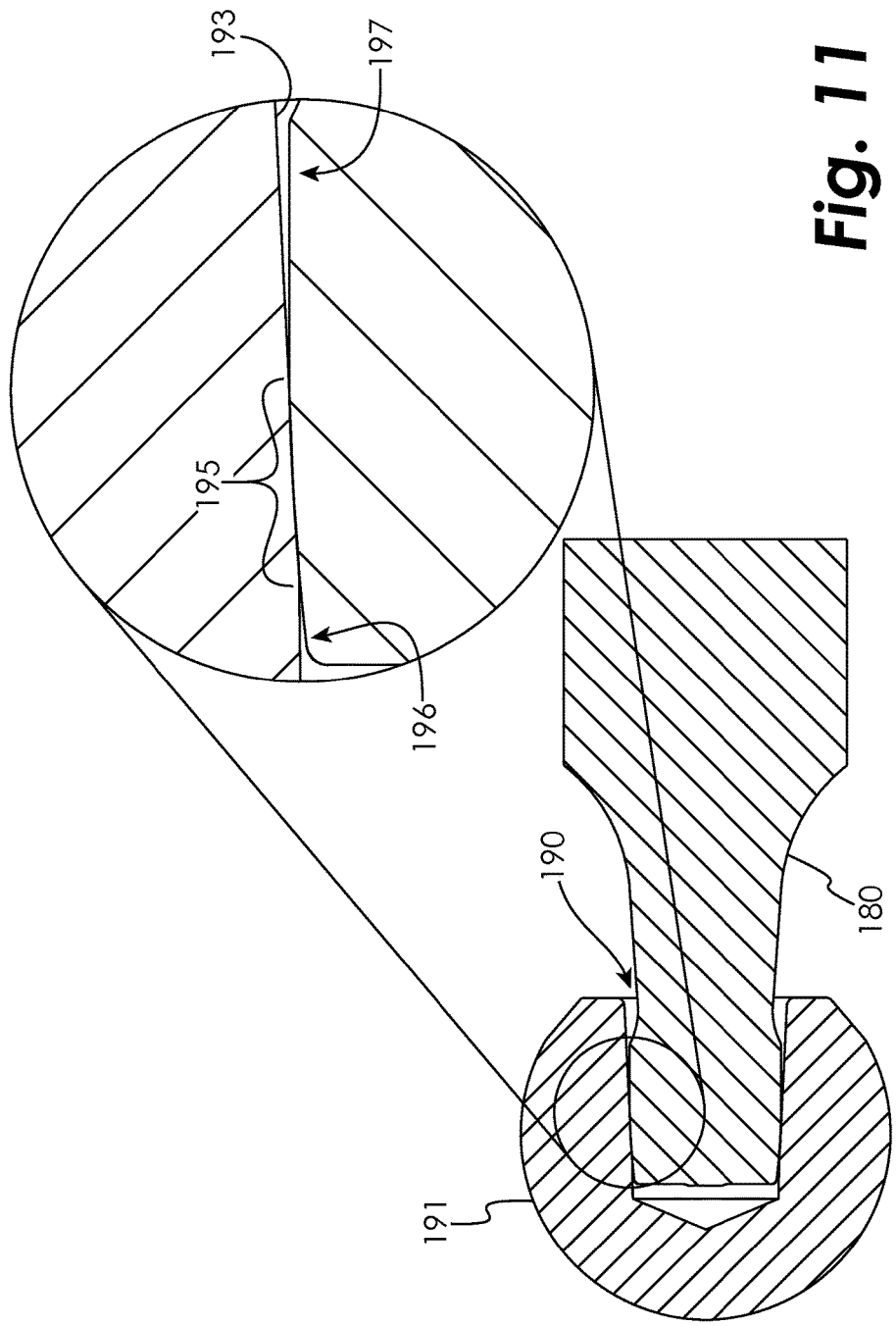
FIG. 11 shows a side view of femoral neck and head components according to one embodiment of the present disclosure.

Turning now to FIG. 11, shown is a partial, side view of a connection made with neck component 180 according to one embodiment of the present disclosure. In particular, neck component 180 is forcibly received in a female bore 190 of a head component 191. An interior wall 193 of the female bore can be tapered generally in relation to the central longitudinal axis of the neck component, for example, having the same or slightly different taper angle than the distal region 182 of the neck component. In this particular embodiment, the angle of the bore is slightly less than that of distal region 182 so that when the neck component is being introduced into the bore in a generally coaxial fashion, initial contact between the free end portion 181 and the interior wall 193 of the bore will occur proximal of the distal-most location 183 of the distal region 182. The exact location(s) of first contact can depend on a number of factors including but not limited to the shape and size of the bore and the relative shapes and sizes of the distal and proximal regions of the free end portion and their spatial orientations relative to one another along the neck component. In some preferred embodiments, when proximal region 186 is made to be tangent or nearly tangent to the straight taper of the distal region 182 at location 188, first contact can occur at or around (e.g., just proximal or just distal to) location 188. Thereafter, once a tight and secure connection is made as shown in FIG. 11, a securing zone 195 can encompass location 188 (e.g., and extend a distance distally and/or proximally of location 188 along the free end portion 181), and securing zone 195 can be flanked by a first non-securing zone 196 and a second non-securing zone 197. First non-securing zone 196 is located distally of securing zone 195 yet still includes portions of the distal region 182 of the free end portion 181, while the second non-securing zone 197 is proximal of securing zone 195. Any of the forms of contact disclosed herein for securing two objects together, or at least helping to secure them together, can occur in securing zone 195 such as including one or more deformed surface elements on the free end portion 181 and/or walls of the bore 190.

Figure 12:
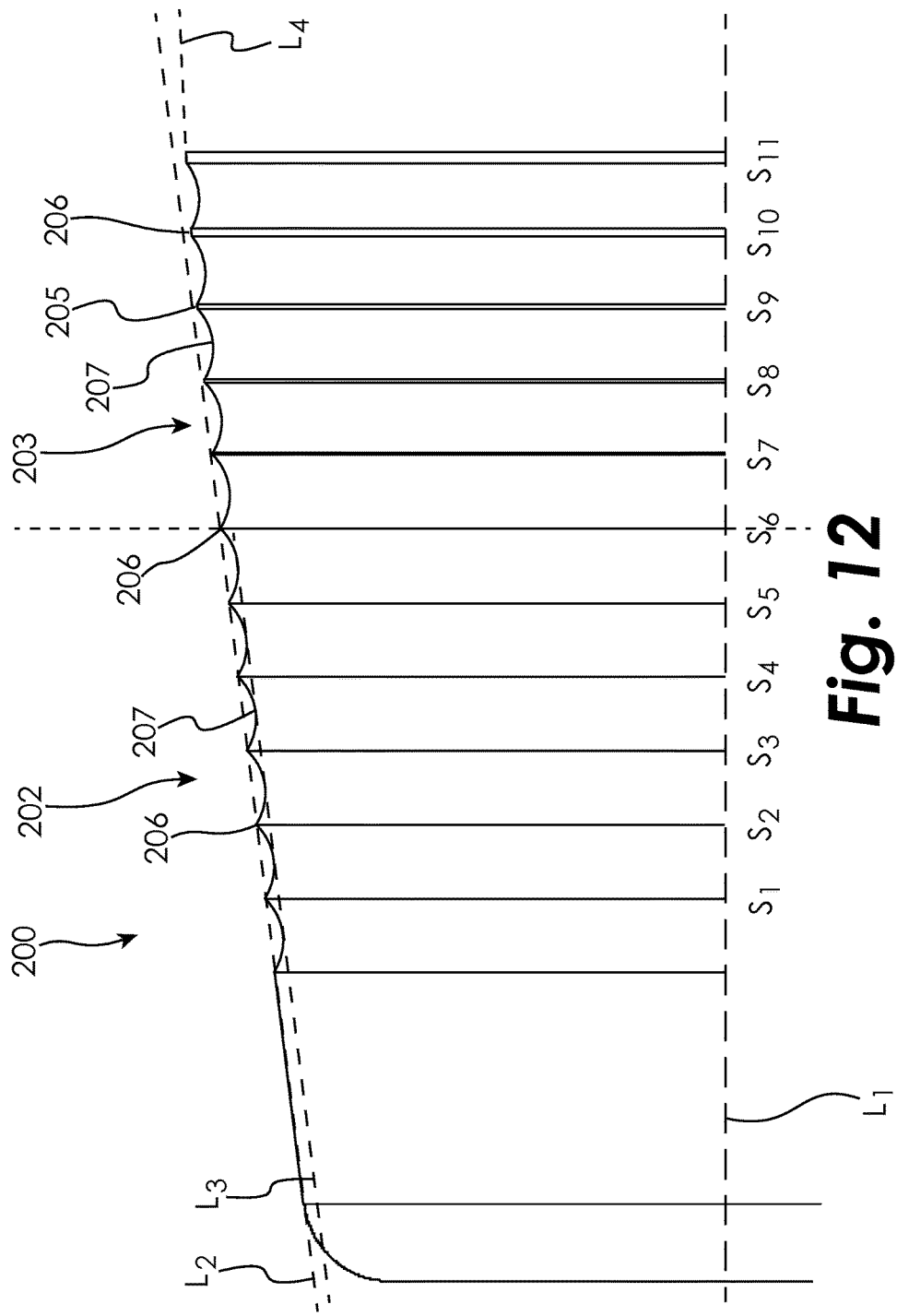
FIG. 12 shows a partial, side view of an orthopedic component according to one embodiment of the present disclosure.

FIG. 12 shows a partial, side view of one example of how deformable surface features can be incorporated into a neck component that is similar to that shown in FIG. 10. In particular, free end portion 200 includes a generally frustoconical distal region 202 and a proximal region 203 with a shape approximating the zone of a sphere or outer surfaces of a torus (e.g., having any suitable radius such as a constant radius in the range of about 100-1,000 mm, or about 200-800 mm, or about 300-700 mm, or about 400-600 mm which may be particularly suitable for some femoral neck embodiments). A series of circumferential and longitudinally successive deformable surface ridges 205 is made to extend over both of these regions. Ridges 205 generally run straight, are parallel to one another, and are perpendicular to, generally perpendicular to, or somewhat angled to the central longitudinal axis of the neck. When angled (e.g., forming part of one or more helical threads along a section or region), such ridges or other deformable surface features can have any suitable pitch or other thread feature or be angled to any suitable degree relative to the central longitudinal axis of the neck. These deformable elements are marked $S_1$-$S_{11}$ in FIG. 12. Of course, more or fewer of these or other deformable surface features could be utilized, and in some embodiments, such deformable surface features additionally or alternatively form part of a wall within a female bore.

When free end portion 200 is viewed from the side as in FIG. 12, a first dashed reference line $L_1$ represents a line running parallel to the central longitudinal axis of the neck, whereas a second dashed reference line $L_2$ and a third dashed reference line $L_3$ (also straight lines like reference line $L_1$) are angled to some degree (e.g., in the range of about 1-6 degrees, or about 2-3.5 degrees) relative to the central longitudinal axis of the neck. While the angle shown may be useful in some embodiments, it has been exaggerated upward to more clearly show the features involved. The deformable surface ridges 205 include peaks 206 and valleys 207, and in distal region 202, the peaks 206 are generally located along the second dashed reference line $L_2$, and the valleys 207 are generally located along the third dashed reference line $L_3$. In this instance, while the overall width or diameter of distal region 202 increases moving in a proximal direction, the height of the peaks 206 as measured from the floor of the valleys 207, and the width of the peaks and valleys, remain generally constant in this region. This sort of arrangement can be accomplished, for example, by threading the distal region 202 with a threading tool having the same approximate taper angle as the distal region.

Continuing with FIG. 12, in proximal region 203, the peaks are generally located along a fourth dashed reference line $L_4$ which has a curved or convex profile when viewed from side to generally give the proximal region 203 a shape approximating the zone of a sphere or outer surfaces of a torus. While not necessary to broader aspects of the disclosure, in this particular embodiment, the fourth dashed reference line $L_4$ is tangent to the second dashed reference line $L_2$ at a location generally corresponding to the peak of deformable surface ridge $S_6$. Then, moving in a proximal direction from ridge $S_6$ to ridge $S_{11}$, the width of the peaks 206 gradually increases, while the height of the peaks as measured from the floor of the valleys, gradually decreases. Coinciding with these changes in peak width are corresponding changes in the width of the valleys 207 situated between successive peaks. As discussed elsewhere herein, a set of deformable surface ridges having the differential peak and valley attributes set forth in FIG. 12 can be formed in any suitable manner including by cutting away, grinding away or otherwise removing material from an initial work piece to provide one or more deformable surface elements, or by welding, adhering or otherwise adding material to an existing piece to provide one or more deformable surface elements, or by casting or otherwise initially forming a component (e.g., using an additive manufacturing process) to have one or more deformable surface elements.

As discussed elsewhere herein, a male-type component (e.g., femoral neck) incorporating such a free end portion 200 can be forcibly received in a female bore of another component (e.g., a femoral head component) to make a secure orthopedic connection. The interior of the female bore can be shaped and configured in a variety of fashions in this regard. In some embodiments, walls of the bore will be tapered generally in relation to the central longitudinal axis of the male-type component, for example, having the same or slightly different taper angle than the distal region 202 of the neck component (e.g., in the range of about 1-6 degrees, or about 2-3.5 degrees). While not required, in some preferred embodiments, the bore will be shaped and sized so that when the neck component is being introduced into the bore in a generally coaxial fashion, initial contact between the free end portion 200 and interior walls or surfaces of the bore will occur at or around deformable surface ridge $S_6$. This sort of initial contact might be accomplished, for example, by having a straight-taper bore that is angled slightly less than that of distal region 202. Nonetheless, it will be understood that the components can be shaped so that initial contact additionally or alternatively occurs at locations that are distal or proximal of ridge $S_6$. The materials involved are such that this contact will partially crush or otherwise deform ridge $S_6$ as the free end portion and the interior walls or surfaces of the female bore are forced longitudinally along and against one another. Thereafter, one or more additional ridges can be deformed in either or both directions to make a tight and secure connection, and in this regard, a securing zone can encompass any number of the deformable surface ridges 205 that have been deformed, and such a securing zone can occur adjacent one or more non-securing zones, e.g., as shown in FIG. 11. Such disclosures should make it clear that outcomes such as the exact location(s) of first contact, type or contact, amount of contact, timing of contact of any of the ridges, etc. can depend on a number of factors including but not limited to the shape and size of the bore and the relative shapes and sizes of the distal and proximal regions of the free end portion and their spatial orientations relative to one another along the male-type component.

All publications cited herein are hereby incorporated by reference in their entirety as if each had been individually incorporated by reference and fully set forth.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

What is claimed is:

1. An orthopedic connection connecting a first orthopedic component to a second orthopedic component, the orthopedic connection comprising:
a male-type connecting member projecting from the first orthopedic component and having a general longitudinal axis; and
a female-type aperture situated in the second orthopedic component and in forcible receipt of the male-type connecting member so as to create a securing zone in which a portion of the male-type connecting member makes forcible contact with walls of the female-type aperture and maintains said forcible contact to securely connect the first orthopedic component to the second orthopedic component,
wherein the male-type connecting member includes a distal longitudinal segment and a proximal longitudinal segment,
wherein in a single reference plane that includes said general longitudinal axis the distal longitudinal segment extends in a linear fashion and the proximal longitudinal segment extends in a curvilinear fashion, wherein the distal longitudinal segment adjoins the proximal longitudinal segment at a first location along the male-type connecting member,
wherein the portion of the male-type connecting member that makes forcible contact with walls of the female-type aperture and maintains said forcible contact encompasses the first location and extends distally and proximally of the first location along the male-type connecting member so that the portion includes a part of the distal longitudinal segment and a part of the proximal longitudinal segment,
wherein the female-type aperture being in forcible receipt of the male-type connecting member includes a first non-securing zone in which the distal longitudinal segment of the male-type connecting member is present but the walls of the female-type aperture are not contacted by the distal longitudinal segment, the first non-securing zone located distally of the securing zone,
wherein the female-type aperture being in forcible receipt of the male-type connecting member also includes a second non-securing zone in which the proximal longitudinal segment of the male-type connecting member is present but the walls of the female-type aperture are not contacted by the proximal longitudinal segment, the second non-securing zone located proximally of the securing zone.

2. The orthopedic connection of claim 1, wherein the first orthopedic component is a femoral neck and the second orthopedic component is a femoral head.

3. The orthopedic connection of claim 1, wherein the proximal longitudinal segment includes one or more deformable surface elements that are deformed by the portion of the male-type connecting member making forcible contact with walls of the female-type aperture and maintaining said forcible contact.

4. The orthopedic connection of claim 1, wherein the proximal longitudinal segment is tangent to the distal longitudinal segment at the first location.

5. The orthopedic connection of claim 1, wherein said curvilinear fashion has a constant radius.

6. The orthopedic connection of claim 1, wherein two or more successive circumferential grooves extend over at least part of said proximal longitudinal segment and over at least part of said distal longitudinal segment.

7. The orthopedic connection of claim 1, wherein the distal longitudinal segment and the proximal longitudinal segment each include multiple successive surface ridges in the single reference plane, and wherein the securing zone includes more than one crushed surface ridge of the distal longitudinal segment and more than one crushed surface ridge of the proximal longitudinal segment.

8. An orthopedic connection connecting a first orthopedic component to a second orthopedic component, the orthopedic connection comprising:
a male-type connecting member projecting from the first orthopedic component and having a general longitudinal axis; and
a female-type aperture situated in the second orthopedic component and in forcible receipt of the male-type connecting member so as to create a securing zone in which a portion of the male-type connecting member makes forcible contact with walls of the female-type aperture and maintains said forcible contact to securely connect the first orthopedic component to the second orthopedic component,
wherein the male-type connecting member includes a distal longitudinal segment and a proximal longitudinal segment,
wherein in a single reference plane that includes said general longitudinal axis the distal longitudinal segment extends in a linear fashion and the proximal longitudinal segment extends in a curvilinear fashion,
wherein the distal longitudinal segment adjoins the proximal longitudinal segment at a first location along the male-type connecting member, wherein the portion of the male-type connecting member that makes forcible contact with walls of the female-type aperture and maintains said forcible contact encompasses the first location and extends distally and proximally of the first location along the male-type connecting member so that the portion includes a part of the distal longitudinal segment and a part of the proximal longitudinal segment,
wherein the female-type aperture being in forcible receipt of the male-type connecting member includes a first non-securing zone in which the distal longitudinal segment of the male-type connecting member is present but the walls of the female-type aperture are not contacted by the distal longitudinal segment, the first non-securing zone located distally of the securing zone,
wherein the female-type aperture being in forcible receipt of the male-type connecting member also includes a second non-securing zone in which the proximal longitudinal segment of the male-type connecting member is present but the walls of the female-type aperture are not contacted by the proximal longitudinal segment, the second non-securing zone located proximally of the securing zone, and
wherein the part of the proximal longitudinal segment that is included in the portion of the male-type connecting member making forcible contact with walls of the female-type aperture and maintaining said forcible contact is at least partially threaded.

9. The orthopedic connection of claim 8, wherein the distal longitudinal segment is at least partially threaded.

10. An orthopedic connection for connecting a first orthopedic component to a second orthopedic component, the orthopedic connection comprising:
a male-type connecting member projecting from the first orthopedic component and having a general longitudinal axis; and a female-type aperture situated in the second orthopedic component and in forcible receipt of the male-type connecting member so as to create a securing zone in which a portion of the male-type connecting member makes forcible contact with walls of the female-type aperture and maintains said forcible contact to securely connect the first orthopedic component to the second orthopedic component, wherein the male-type connecting member includes a continuously threaded longitudinal segment with a distal region and a proximal region, wherein in a single reference plane that includes said general longitudinal axis the distal region includes a first set of successive thread peaks extending in a linear fashion and the proximal region includes a second set of successive thread peaks extending in a curvilinear fashion, wherein the distal region adjoins the proximal region at a first location along the continuously threaded longitudinal segment, wherein the portion of the male-type connecting member that makes forcible contact with walls of the female-type aperture and maintains said forcible contact encompasses the first location and extends distally and proximally of the first location along the continuously threaded longitudinal segment so that the portion includes a first distal group of crushed thread peaks from the first set of successive thread peaks and a first proximal group of crushed thread peaks from the second set of successive thread peaks, respectively, wherein the female-type aperture being in forcible receipt of the male-type connecting member includes a first non-securing zone in which a second distal group of thread peaks from the first set of successive thread peaks are present but the walls of the female-type aperture are not contacted by the second distal group of thread peaks from the first set of successive thread peaks, the first non-securing zone located distally of the securing zone, wherein the female-type aperture being in forcible receipt of the male-type connecting member also includes a second non-securing zone in which a second proximal group of thread peaks from the second set of successive thread peaks are present but the walls of the female-type aperture are not contacted by the second proximal group of thread peaks from the second set of successive thread peaks, the second non-securing zone located proximally of the securing zone.

11. The orthopedic connection of claim 10, wherein the male-type connecting member includes a non-threaded longitudinal segment located distally of said threaded longitudinal segment.

12. The orthopedic connection of claim 10, wherein said first orthopedic component is a femoral neck component.

13. The orthopedic connection of claim 10, wherein said curvilinear fashion has a constant radius.

* * * * *